US009192536B2

(12) United States Patent
Mackin et al.

(10) Patent No.: US 9,192,536 B2
(45) Date of Patent: Nov. 24, 2015

(54) CODE SUPPORT DEVICE FOR INFANT CARE DEVICES

(75) Inventors: Michael H. Mackin, Ellicott City, MD (US); Christopher A. Dykes, Columbia, MD (US); Lynn E. Bayne, Kingsville, MD (US)

(73) Assignee: Segars California Partners, LP, Austin, TX (US)

( * ) Notice: Subject to any disclaimer, the term of this patent is extended or adjusted under 35 U.S.C. 154(b) by 0 days.

(21) Appl. No.: 13/475,768

(22) Filed: May 18, 2012

(65) Prior Publication Data

US 2013/0307697 A1   Nov. 21, 2013

(51) Int. Cl.
*G08B 1/08* (2006.01)
*A61G 11/00* (2006.01)
*G06Q 50/22* (2012.01)
*G06F 19/00* (2011.01)

(52) U.S. Cl.
CPC ............ *A61G 11/00* (2013.01); *G06F 19/3487* (2013.01); *G06Q 50/22* (2013.01); *G06F 19/3468* (2013.01)

(58) Field of Classification Search
USPC ............... 340/500, 573.1, 691.1–691.6, 328, 340/384.1, 815.4; 600/21, 22, 500–509, 600/523, 529, 300; 5/600, 655
See application file for complete search history.

(56) References Cited

U.S. PATENT DOCUMENTS

| | | | |
|---|---|---|---|
| 7,038,588 B2 * | 5/2006 | Boone et al. ............... | 340/573.1 |
| 7,966,678 B2 | 6/2011 | Ten Eyck | |
| 2002/0196141 A1 | 12/2002 | Boone | |
| 2006/0187628 A1 * | 8/2006 | Le et al. ........................ | 361/683 |
| 2007/0185736 A1 * | 8/2007 | Cervi et al. ...................... | 705/2 |
| 2008/0053445 A1 * | 3/2008 | Kroupa et al. ........... | 128/205.23 |
| 2009/0149927 A1 * | 6/2009 | Kneuer et al. .................. | 607/96 |
| 2012/0232357 A1 * | 9/2012 | Coelho ......................... | 600/301 |

\* cited by examiner

*Primary Examiner* — Travis Hunnings
(74) *Attorney, Agent, or Firm* — M. A. Ervin & Associates; Michael A. Ervin

(57) ABSTRACT

A code support device providing emergency code displays for caregivers responsible for infant patients in an infant care device. The code support device has a graphic user interface display for gathering, recording and displaying information used in the routine operation of the infant care device and when needed displays a code screen in response to an emergency situation that directs caregivers through a preprogrammed emergency code of activity to respond to the emergency.

20 Claims, 2 Drawing Sheets

CODE SUPPORT DEVICE FOR INFANT CARE DEVICES

FIELD OF THE INVENTION

The present invention relates to an apparatus for providing special capabilities to caregivers during emergencies involving infants in infant care devices.

BACKGROUND OF THE INVENTION

A code is medical slang for a situation where a patient experiences cardiopulmonary arrest, requiring a team of providers (sometimes called a "Code team") to rush to the specific location and begin immediate resuscitative efforts. It is not uncommon for an infant patient to experience a Code following delivery or while being cared for in an intensive care area. The Code team ideally consists of 4-6 people, each with defined roles, though often fewer are available. A Code is an intense period of time involving many people that can have very serious consequences. An infant radiant warmer is often the platform on which an infant code is treated.

There are many actions the Code team is responsible for during a code. The infant may require warming, airway suctioning, oxygen, pulmonary resuscitation, chest compression, drugs, or other care. Individual members of the team are responsible for specific tasks, e.g. manual resuscitation, cardiac massage, drug preparation, etc. Usually, if available, one individual is responsible for keeping a record of the activities and the time they take place. Some hospitals are making video records of a code and using these as a tool for post code analysis for the purpose of improving code team performance and patient outcome.

This invention provides a valuable tool that assist the code team in performing their task.

SUMMARY OF THE INVENTION

This valuable tool is provided by a code support device providing emergency code displays for caregivers responsible for infant patients in an infant care device including at least; a graphic user interface display connected to the code support device and adapted to display desired information used in the routine operation of the infant care device as well as code support information; an internal processor in the code support device adapted to accept programming to gather information, store that information in memory, and send desired information to the graphic user interface; wherein the graphic user interface display is preprogrammed to display a code screen in response to an emergency situation that directs caregivers through a preprogrammed emergency code of activity to respond to the emergency.

The description that follows envisions a code support device connected to an infant care device with a controller, a display and provision for the user to interact with the controller through discrete switches, a touch panel, a keyboard or voice commands. In the context of this application the term infant care device can be any modality that supports an infant in a medical environment. This is often an infant warmer, but could be an incubator or any type of infant bed or heated bed system. The preferred embodiment of this invention envisions the code support device connected to the infant care device and with a display with integral touch pad the size of a tablet computer or iPad. Further the preferred device has a touch pad area labeled Code that when touched brings up a code screen with the following elements.

a timeline showing the time since the code began.
touch pad recording of activities along the timeline, e.g. begin chest compressions.
a chart of the code drugs dose, ET tube diameter and length by infant weight.
Audible pacing commands for resuscitation and chest compressions
initiation of video recording
the ability to save, transfer and print a record of the code The problem of rapidly and effectively carrying out a code team effort in a stressful situation is addressed by a code support device providing emergency code displays for caregivers responsible for infant patients in an infant care device including at least; a graphic user interface display connected to the code support device and adapted to display desired information used in the routine operation of the infant care device as well as code support information; an internal processor in the code support device adapted to accept programming to gather information, store that information in memory, and send desired information to the graphic user interface; wherein the graphic user interface display is preprogrammed to display a code screen in response to an emergency situation that directs caregivers through a preprogrammed emergency code of activity to respond to the emergency, provides important information to the caregiver, such as time since start of code, appropriate catheter and tube size, and convenient recording of significant interventions, such as intubation, chest compression, and drug administration. The code support device provides a record of code activity for post code analysis and as required for inclusion in the patient's medical record; this record might contain start time of code, time of intubation, time of chest compressions, SPO2 and HR values, drugs or fluids delivered and timing, etc.

BRIEF DESCRIPTION OF THE DRAWINGS

Other objects, features, and advantages of the present invention will be apparent from the written description and the drawings in which.

DETAILED DESCRIPTION OF THE INVENTION

The preferred embodiment of this invention is a code support device associated with infant care device and having a large (10 inch diagonal or greater) graphic user interface display. A smaller screen is possible but not desirable. The code support device is equipped with an internal processor and adapted to accept programming to display desired information. The code support device is also associated with the infant care device in order to gather, record in memory, and display desired information used in the routine operation of the infant warmer. This code support device may be a part of the infant care device and may use the graphic user interface in displaying routine operation of the infant care device as well as code support information. This information gathered includes but is not limited to temperatures of the warmer and the patient, weight of the patient, heart rate of the patient, the saturation of peripheral oxygen number of the patient, which is a measure of the amount of oxygen attached to the hemoglobin cell of the patient, etc. The infant care device may have a built in weighing scale and the ability to store weights that are measured.

Figure 1:
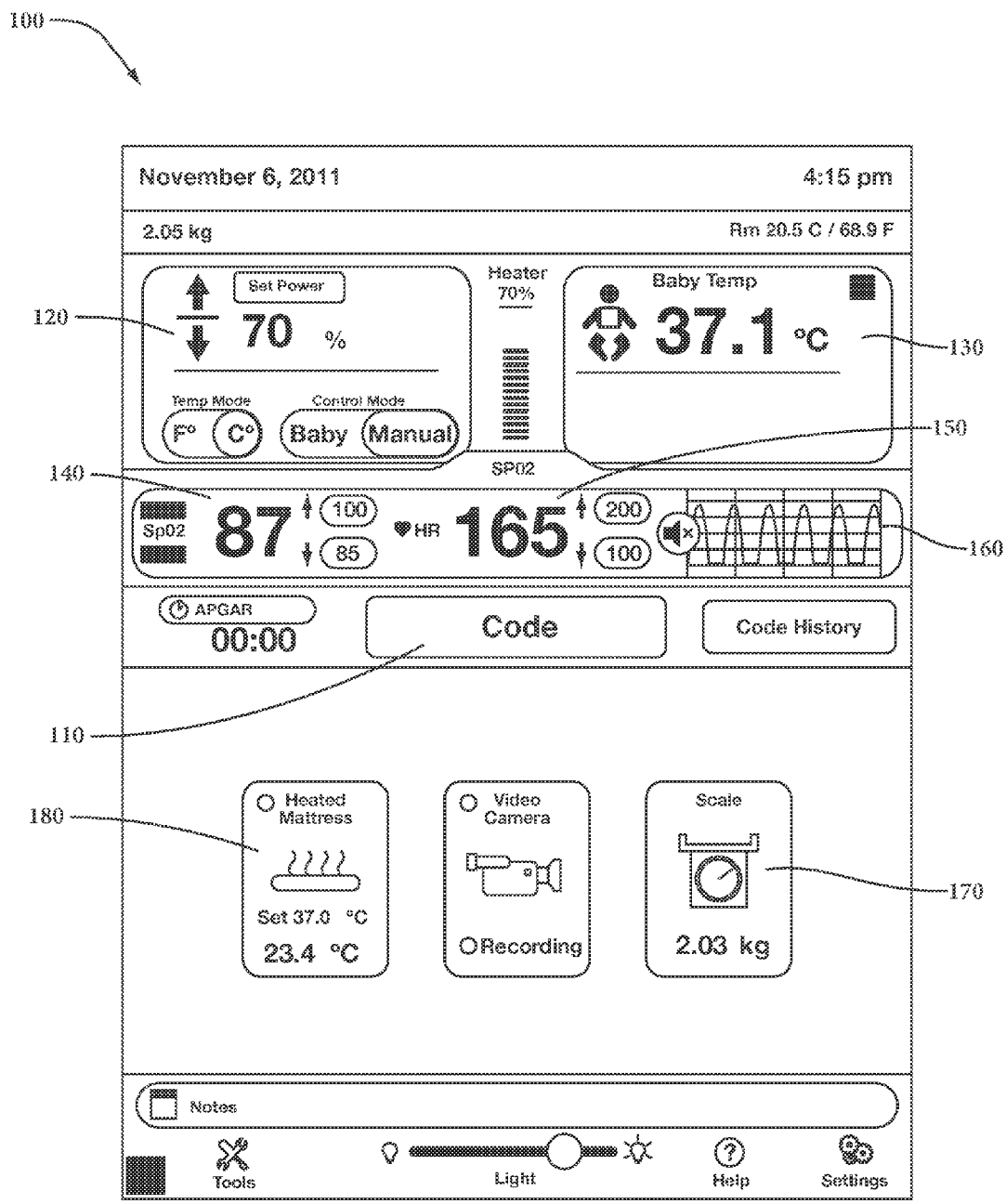
FIG. 1 is an illustration of a possible home screen of the code support device.

The home screen of the device could have multiple possible screens in which some of the screens have a touch-activated switch labeled "Code". FIG. 1 illustrates what a possible home screen, indicated by the numeral 100, might look like. The actual arrangement of the display is not critical. The infant care device is not shown. The "Code" button 110 is in the center of this screen. The other functions 120, 130, 140, 150, 160, 170, 180, shown in FIG. 1 are important to monitoring an infant care device but part of the prior art and is not part of this inventive concept.

Figure 2:
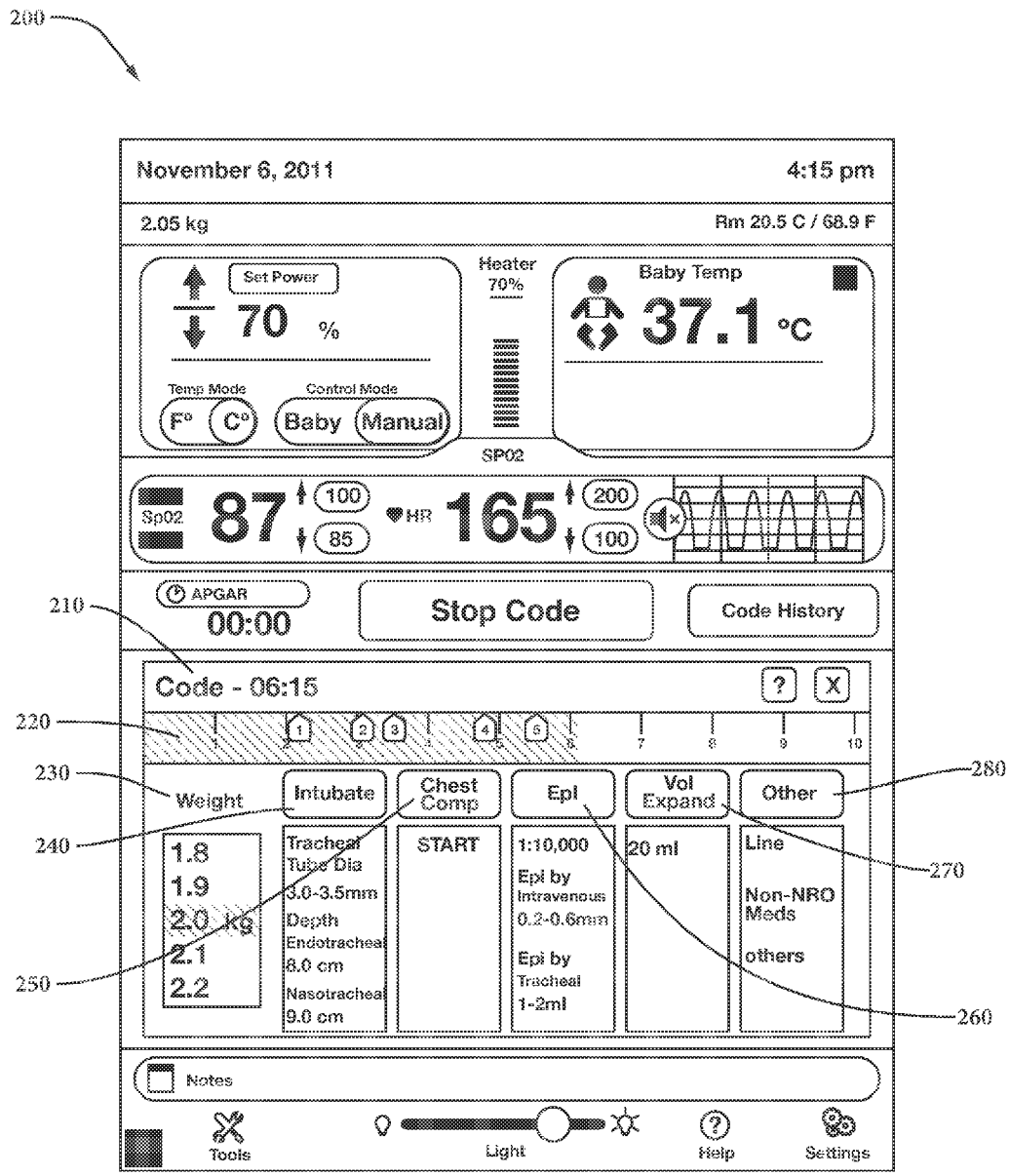
FIG. 2 is an illustration of a possible displayed code screen that is displayed after the CODE button is pushed on the screen of FIG. 1

When Code button 110 is touched, the complete display is programmed to automatically change to a second screen called the Code screen. FIG. 2, shown as the numeral 200, is an illustration of how this Code screen might look. The Code screen is the lower half of the display in this example.

As envisioned, the code screen displays the following information:

- The time 210 that has elapsed since the code button was activated.
- A timeline 220 that provides visual indication of how long the code has been in progress. The time often seems shorter than it actual is during this emergency situation.
- The weight of the patient 230.
- A calculator (not shown) that provides recommended intubation tube diameter and depth of placement, dosage of any drugs or fluids based on patient weight. Weight can be adjusted by the user and the device will provide values for these based upon recommendations from the American Academy of Pediatrics and others. If the patient has been weighed on the infant care device scale previous to the Code, the initial weight input to the calculator will be that weight.
- Color coded touch pads for Intubate 240, Chest Compression 250, Epinephrine 260, Volume Expander 270, and Other 280 on the code screen which when pressed place a color coded marker on the timeline identifying what time a particular event occurred. These can be arranged in the order they are typically experienced in a code event. Additional drugs or fluids other than epinephrine or volume expander could have touch pads.
- The ability to record the doses of drugs or fluids administered.
- The recording of pulse rate and saturation oxygen during the code.
- The silencing of alarms during the code.
- The automatic activation of a video recorder focused on the patient bed at the time of the code initiation.
- Automatic activation of audio pacing for pulmonary resuscitation after the Intubation button is touched. This audio pacing may be tone based or voice based.
- Automatic activation of audio pacing for cardiac compression after the Chest Compression button is touched. This audio pacing may be tone based or voice based.
- The ability to save the record of this code for future reference.
- The ability to save the video and audio record of the code.
- The ability to print the record of this code.
- The ability to transfer code records including the video though a digital port to the hospital information system, a memory stick or other digital device.

The five buttons (Intubate, Chest Comp, Epi, Vol Expand, and Other illustrate key code events whose time(s) are recorded during a code event. Often an additional staff person is present to record those events. With the graphic user interface described herein simply touching those buttons as the events occur makes those recordings. Other drugs or fluids than epinephrine or volume expander are possible and the inventive concept anticipates them.

The graphic user interface can alternately be programmed to accept voice commands to record these same events.

In operation the code support device display could be in a first mode of operation in which through its connectedness to the infant care device it is able to display any or all of the variables associated with operation of the infant care device. In this first preprogrammed mode the interactive touch screen display is also able to accept commands from a caregiver through the graphic user interface to adjust certain of the variables of the infant care device.

The code support device can also be preprogrammed to accept a command from the touch screen to switch to a second mode of operation in which it displays a "Code" screen that is preprogrammed to display useful information to guide the caregiver through the recommended response to an emergency situation.

It is important to understand that the code support device could be dedicated to the Code screen functionality only and not have any additional functions related to the routine operation of the infant care device.

The term "Code" is generally used to indicate a situation in which a patient requires resuscitation or otherwise in need of immediate medical attention, most often as the result of a respiratory arrest or cardiac arrest.

The Code screen could have a time indicator displaying time elapsed after the beginning of the code response and a timeline showing events that transpire during the code.

A frequently used code intervention in respiratory or cardiac arrest is intubation, the placement of a flexible plastic or rubber tube into the windpipe to maintain an open airway or to serve as a conduit through which to administer certain drugs. The proposed code screen could have a recommendation for intubation parameters for an infant and a button to push when the intubation procedure is done. This would then place a marker on the timeline.

Another common intervention is chest compression. This appears on the screen shown in FIG. 2. Again pressing the Chest Compression button places another marker on the timeline.

Another common intervention is an injection of epinephrine (adrenaline) for cardiac arrest. The code screen can be programmed to calculate the recommended dosage based on the weight of the infant, which is already a known variable from the weigh scale in the infant care device. FIG. 2 shows a display of this recommendation. Again after injection the button can be pushed to record it on the timeline.

Another common intervention is an intravenous therapy called a Volume Expander. This provides additional fluid volume for the circulatory system. FIG. 2 shows a display of this reminder as well as a recommended amount. Again after injection the button can be pushed to record it on the timeline.

Other interventions can be displayed on the Code screen based on the recommended "Code Team" actions at any hospital or caregiver facility.

It is required that the code team produce an accurate record of the procedures performed, drugs administered, and timing of each event for the patient medical record. The internal processor can be programmed to assemble such a record and provide it as an output to a printer, memory stick, personal computer, or hospital IT system.

Although a graphic user interface has been described for this code screen interface, it is also conceived that many of these actions could be voice activated.

The foregoing description is of a preferred embodiment for implementing the invention, and the scope of the invention should not be limited by this description. The scope of the present invention is instead defined by the following claims.

The invention claimed is:

1. A code support device providing emergency code displays for caregivers responsible for infant patients in an infant care device, comprising;
   a. a graphic user interface display connected to said code support device and adapted in a first mode to display desired information used in the routine operation of the infant care device as well as code support information;
   b. an internal processor in said code support device adapted to accept programming to gather information, store that information in memory, and send desired information to said graphic user interface;
   c. wherein in this first mode a touch activated switch is available to convert the user interface display to a second mode;
   d. wherein in the second mode said graphic user interface display is preprogrammed to display an emergency code screen in response to an emergency situation that directs caregivers through a preprogrammed recommended response of activity to the emergency situation;
   e. wherein said recommended response comprises one or more of recommended intubation parameters, recommended dosages of epinephrine, and recommended volumes of intravenous volume expander therapy.

2. The code support device providing emergency code displays for caregivers responsible for infant patients in an infant care device of claim 1 wherein the emergency code screen displays the elapsed time since the code response is initiated.

3. The code support device providing emergency code displays for caregivers responsible for infant patients in an infant care device of claim 1 wherein the emergency code screen displays a timeline that provides visual indication of how long the code has been in progress.

4. The code support device providing emergency code displays for caregivers responsible for infant patients in an infant care device of claim 1 wherein the emergency code screen may display the recommended intubation tube size and depth of placement guidelines for infants by calculation based on medical guidelines and on a weight of the infant determined by the emergency code support device or on a weight entered by a user.

5. The code support device providing emergency code displays for caregivers responsible for infant patients in an infant care device of claim 1 wherein the emergency code screen automatically calculates the correct amount of a drug or fluid to be administered based on medical guidelines and a weight of the infant determined by the code support device or on a weight entered by a user.

6. The code support device providing emergency code displays for caregivers responsible for infant patients in an infant care device of claim 1 wherein the graphic user interface display is programmed with the ability to record the placement of an intubation tube or dose of drug or fluid administered during the emergency code and the time they were delivered.

7. The code support device providing emergency code displays for caregivers responsible for infant patients in an infant care device of claim 1 wherein the code support device is programmed with the ability to record pulse rate and saturation oxygen during the emergency code.

8. The code support device providing emergency code displays for caregivers responsible for infant patients in an infant care device of claim 1 wherein the code support device is programmed with the ability to silence alarms during the emergency code.

9. The code support device providing emergency code displays for caregivers responsible for infant patients in an infant care device of claim 1 wherein the code support device is programmed with the ability to activate a video recorder focused on the patient bed at the time of the emergency code initiation.

10. The code support device providing emergency code displays for caregivers responsible for infant patients in an infant care device of claim 1 wherein the graphic user interface display is programmed with the ability to automatically activate audio pacing for pulmonary resuscitation during the emergency code.

11. The code support device providing emergency code displays for caregivers responsible for infant patients in an infant care device of claim 1 wherein the code support device is programmed with the ability to save the record of an emergency code for future reference.

12. The code support device providing emergency code displays for caregivers responsible for infant patients in an infant care device of claim 1 wherein the code support device is programmed with the ability to print the record of the emergency code.

13. The code support device providing emergency code displays for caregivers responsible for infant patients in an infant care device of claim 1 wherein the code support device is programmed with the ability to transfer emergency code records including a video record though a digital port to the hospital information system, a memory stick or other digital device.

14. The code support device providing emergency code displays for caregivers responsible for infant patients in an infant care device of claim 1 wherein the code support device is programmed with the ability to assist in recording the time of emergency code events.

15. The code support device providing emergency code displays for caregivers responsible for infant patients in an infant care device of claim 14 wherein the pressing of a code button records the time of defined emergency code events.

16. The code support device providing emergency code displays for caregivers responsible for infant patients in an infant care device of claim 14 wherein said defined emergency code events may include the time when the infant is intubated, the start and or stop time of chest compressions, the time when drugs or fluids are administered, or other predefined events.

17. The code support device providing emergency code displays for caregivers responsible for infant patients in an infant care device of claim 14 wherein a voice command initiates the recording the time of defined emergency code events.

18. The code support device providing emergency code displays for caregivers responsible for infant patients in an infant care device of claim 17 wherein said defined emergency code events may include the time when the infant is intubated, the start and or stop time of chest compressions, the time when drugs or fluids are administered, or other predefined events.

19. The code support device providing emergency code displays for caregivers responsible for infant patients in an infant care device of claim 1 wherein the code support device is an integral part of the infant care device.

20. The code support device providing emergency code displays for caregivers responsible for infant patients in an infant care device of claim 1 wherein the code support device is separate but communicates with the infant care device.

* * * * *